United States Patent [19]
Kato et al.

[11] Patent Number: 5,578,732
[45] Date of Patent: Nov. 26, 1996

[54] PRODUCTION OF 2-(2-PYRIDYLMETHYLSULFINYL) BENZIMIDAZOLE COMPOUNDS BY SELECTIVE OXIDATION IN THE PRESENCE OF A VANADIUM CATALYST

[75] Inventors: Masayasu Kato, Hyogo; Yoshio Toyoshima; Norio Iwano, both of Osaka, all of Japan

[73] Assignee: Takeda Chemical Industries, Ltd., Osaka, Japan

[21] Appl. No.: 430,178

[22] Filed: Apr. 27, 1995

Related U.S. Application Data

[63] Continuation of Ser. No. 68,320, May 28, 1993, abandoned, which is a continuation of Ser. No. 759,651, Sep. 13, 1991, abandoned, which is a continuation of Ser. No. 222,424, Jul. 21, 1988, abandoned.

[30] Foreign Application Priority Data

Jul. 21, 1988 [JP] Japan ................... 62-194809

[51] Int. Cl.$^6$ ............ C07D 401/06; C07D 401/12
[52] U.S. Cl. ................................................ 546/273.7
[58] Field of Search ............................................. 546/271

[56] References Cited

U.S. PATENT DOCUMENTS

| | | | |
|---|---|---|---|
| 4,255,431 | 4/1979 | Junggren et al. | 546/271 |
| 4,555,518 | 11/1985 | Rainer | 546/271 |
| 4,628,098 | 12/1986 | Nohara et al. | 546/271 |
| 4,727,150 | 2/1988 | Nohara et al. | 546/271 |
| 4,738,975 | 4/1988 | Nohara et al. | 546/271 |

FOREIGN PATENT DOCUMENTS

| | | | |
|---|---|---|---|
| 0302720 | 2/1969 | European Pat. Off. | 546/271 |
| 0005129 | 10/1979 | European Pat. Off. | 546/271 |
| 005129B1 | 4/1981 | European Pat. Off. | 546/271 |
| 0080602 | 6/1983 | European Pat. Off. | 546/271 |
| 0175464 | 3/1986 | European Pat. Off. | 546/271 |
| 0174726 | 3/1986 | European Pat. Off. | 546/271 |
| 2336817 | 2/1974 | Germany | 546/271 |

OTHER PUBLICATIONS

Bird, Anne: The synthesis of omeprazole: A study of alternative routes for the conversion from H 168/22 to H 168/68. M.Sc degree project report, KTH 1983. pp. 18,24,26–28.

Madesclaire, Michel: Synthesis of sulfoxides by oxidation of thioethers. Tetrahedron vol. 42, No. 20, 5459–5495, 1986. pp. 5461–5462.

Gilman, Henry, et al. (eds): Organic Chemistry, An Advanced Treatise, vol. IV. (John Wiley & Sons, Inc., New York 1953). p. 842.

Neville Jones, D. (ed): Comprehensive Organic Chemistry, The Synthesis and Reaction of Organic Compounds. vol. 3 (Pergamon Press, 1979). p. 124.

Organic Sulfur Compounds, vol. I, Pergamon Press 1961, pp. 228–233.

"The Vanadium Pentoxide–catalysed Oxidation of Thio-compounds with Hydrogen Peroxide," *J. Chem. Soc. (C)*, 1969, F. E. Hardy et al., pp. 2334–2336.

*Tetrahedron Report Number 210,* "Synthesis of Sulfoxides by Oxidation of Thioethers," vol. 42, No. 20, pp. 5459–5495, 1986.

C.A. No. 2906h, vol. 60, 1964.
C.A. No. 23480a, vol. 55, 1961.
Tetrahedron, vol. 42, No. 17, 1986, pp. 5459, 5461 and 5462.

Chemical Abstracts, vol. 97, No. 1, Jul. 5, 1982, p. 547, col. 1, abstract No. 5611n. Ogata et al.

Chemical Abstracts, vol. 68, No. 1, Jan. 1, 1968, p. 658, col.2, abstract No. 6741t.

Supplement E, The chemistry of ethers, crown ethers, hydroxy groups and their sulphur analogues, Part 1, Ed. Saul Patai, pp. 539–608, 1980.

Tetrahedron vol. 42, No. 20, pp. 5459–5495 (1986).

*Primary Examiner*—Floyd D. Higel
*Attorney, Agent, or Firm*—Merchant, Gould, Smith, Edell, Welter, Schmidt, P.A.

[57] ABSTRACT

2-(2-pyridylmethylsulfinyl)benzimidazole compounds are produced by subjecting 2-(2-pyridylmethylthio)benzimidazole compounds to oxidation with hydrogen peroxide in the presence of vanadium compounds in good yield and with low production of by-products.

6 Claims, No Drawings

PRODUCTION OF 2-(2-PYRIDYLMETHYLSULFINYL) BENZIMIDAZOLE COMPOUNDS BY SELECTIVE OXIDATION IN THE PRESENCE OF A VANADIUM CATALYST

This application is a continuation of application Ser. No. 08/068,320, filed May 28, 1993 and now abandoned, which is a continuation of application Ser. No. 07/759,651, filed Sep. 13, 1991 and now abandoned, which is a continuation of Ser. No. 07/222,424, filed Jul. 21, 1988 and now abandoned.

This invention relates to the production of 2-(2-pyridylmethylsulfinyl)benzimidazole compounds (refer to, for example, U.S. Pat. No. 4,255,431, European Patent Laid-Open No.45200, No.74341, No.80602, No.5129, No.174726, No.175464, British Patent Laid-Open No.2134523A), which are useful as antiulcer agents.

As a method for production of 2-(2-pyridylmethylsulfinyl)benzimidazole compounds, an oxidation of the corresponding 2-(2-pyridylmethylthio)benzimidazole compounds with m-chloroperbenzoic acid is mentioned (refer to, for example, U.S. Pat. No. 4,255,431, European Patent Laid-Open No.80602).

Generally known methods for production of sulfoxides from sulfides include oxidation with peracid, hydrogen peroxide, iodosobenzene, N-halosuccinimide, tertiary butyl hypochloride, sodium metaperiodate, selenium dioxide, bromine, chlorine, or ozone [Refer to: Saul Patai, The chemistry of ethers, crown ethers, hydroxyl groups and their sulphur analogues, Supplement E, Part 1, p.539–608, John Willey & Sons, An Interscience Publication (1980), Michel Madesclaire, Tetrahedron Report Number 210, "Synthesis of Sulfoxides by Oxidation of Thioethers", Tetrahedron, 42, 5459–5495 (1986)].

However, the specifications or references do not include concrete examples of practical production of 2-(2-pyridylmethylsulfinyl)benzimidazole compounds by oxidation with hydrogen peroxide as the oxidizing agent.

Oxidation of 2-(2-pyridylmethylthio)benzimidazole compounds with m-chloroperbenzoic acid gives 2-(2-pyridylmethylsulfinyl)benzimidazole compounds only in low yields, producing much side products such as 2-(2-pyridylmethylsulfonyl)benzimidazole N-oxide. Such side products are very difficult to remove from 2-(2-pyridylmethylsulfinyl)benzimidazole compounds with usual methods of purification, such as recrystallization. Expensiveness of m-chloroperbenzoic acid is an additional problem.

There are some problems in oxidation of 2-(2-pyridylmethylthio)benzimidazole compounds with one of the oxidizing agents described above other than hydrogen peroxide; the reaction will not proceed in many cases, and the yield is very low (less than about 75%) because of degradation or production of a great amount of by-products.

As the results of the inventors' researches to find a method for production of 2-(2-pyridylmethylsulfinyl)benzimidazole compounds from 2-(2-pyridylmethylthio)benzimidazole compounds in good yield and with low production of by-products such as 2-(2-pyridylmethylsulfonyl)benzimidazole N-oxides, the inventors have found that oxidation with hydrogen peroxide in the presence of vanadium compounds, for example, vanadium oxides or vanadium salts, as the catalyst accomplishes the purpose, and have completed the invention after further researches.

This invention relates to a method for producing a compound having the formula (II):

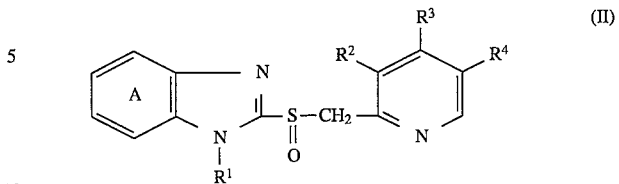

wherein the ring A may be substituted; $R^1$ is a hydrogen atom or an N protective group; $R^2$, $R^3$ and $R^4$ are independently hydrogen atom, an alkyl group which may be fluorinated or an alkoxy group which may be fluorinated, which comprises subjecting a compound having the formula (I):

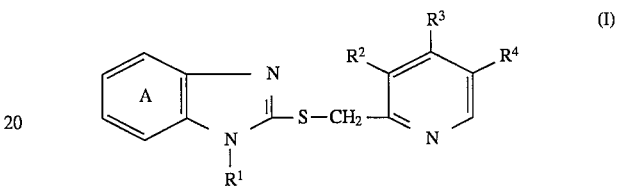

wherein A, $R^1$, $R^2$, $R^3$ and $R^4$ are the same as described above, to oxidation with hydrogen peroxide in the presence of vanadium compounds.

In compounds (I) and (II), the substituents in the ring A include alkyl, halogen, cyano, carboxy, carboalkoxy, carboalkoxyalkyl, carbamoyl, carbamoylalkyl, hydroxy, alkoxy, hydroxyalkyl, trifluoromethyl, acyl, carbamoyloxy, nitro, acyloxy, aryl, aryloxy, alkylthio and alkylsulfinyl etc. The alkyl groups are desirably those having 1 to 7 carbon atoms, including methyl, ethyl, propyl, isopropyl, butyl, isobutyl, pentyl, hexyl and heptyl etc. The halogen atoms include fluorine, chlorine and bromine atoms, among which the fluorine atom is the most desirable. The carboalkoxy groups are desirably those in which the alkoxy group has 1 to 4 carbon atoms, including carbomethoxy ($CH_3OOC-$) and carboethoxy ($C_2H_5OOC-$) etc. The carboalkoxyalkyl groups are desirably those in which the alkoxy and alkyl groups have 1 to 4 carbon atoms each, including carbomethoxymethyl ($CH_3OOCCH_2-$), carbomethoxyethyl ($CH_3OOCC_2H_4-$), carboethoxymethyl ($C_2H_5OOCCH_2-$) and carboethoxyethyl ($C_2H_5OOCC_2H_4-$) etc. The carbamoylalkyl groups are desirably those in which the alkyl group has 1 to 4 carbon atoms, including carbamoylmethyl ($H_2NCOCH_2-$) and carbamoylethyl ($H_2NCOC_2H_4-$) etc. The alkoxy groups are desirably those having 1 to 5 carbon atoms, including methoxy, ethoxy, propoxy, isopropoxy, butoxy, isobutoxy and pentoxy etc. The hydroxyalkyl groups are desirably those in which the alkyl group has 1 to 7 carbon atoms, including hydroxymethyl and 1-hydroxy-propyl-2,1-hydroxyethyl-2,1-hydroxy-2-methyl-propyl-2 etc. The acyl groups are desirably those having 1 to 4 carbon atoms, including formyl, acetyl, propionyl, butylyl and isobutylyl etc. The acyloxy groups are desirably those in which the acyl group has 1 to 4 carbon atoms, including formyloxy, acetyloxy, propionyloxy, butylyloxy, and isobutylyloxy etc. The aryl groups include phenyl, tolyl and naphthyl etc. The aryloxy groups include phenyloxy, tolyloxy and naphthyloxy etc. The alkylthio groups are desirably those in which the alkyl group has 1 to 4 carbon atoms, including methylthio, ethylthio and propylthio etc. The alkylsulfinyl groups are desirably those having 1 to 6 carbon atoms, including methylsulfinyl, ethylsulfinyl and propylsulfinyl etc.

The ring A is not substituted or is substituted at the 4- or 5-position particularly desirably with alkyl, halogen, trifluoromethyl or alkoxy among the substituents described above.

The N-protective groups represented by $R^1$ include alkyl, acyl, carboalkoxy, carbamoyl, alkylcarbamoyl, dialkylcarbamoyl, alkylcarbonylmethyl, alkoxycarbonylmethyl and alkylsulfonyl etc. The alkyl groups are desirably those having 1 to 5 carbon atoms, including methyl, ethyl, propyl, isopropyl, butyl, isobutyl and pentyl etc. The acyl groups include the same groups as those described for the substituents of the ring A. The carboalkoxy groups include the same groups as those described for the substituents of the ring A. The alkylcarbamoyl groups are represented by the formula:

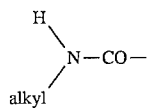

wherein the alkyl group has desirably 1 to 4 carbon atoms, including methylcarbamoyl, ethylcarbamoyl, propylcarbamoyl and isopropylcarbamoyl etc. The dialykylcarbamoyl groups are represented by the formula:

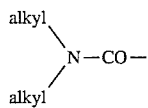

wherein the alkyl groups have desirably 1 to 4 carbon atoms each, including dimethylcarbamoyl, diethylcarbamoyl and N-methyl-N-ethylcarbamoyl etc. The alkylcarbonylmethyl groups are represented by the formula: alkyl-$COCH_2$— wherein the alkyl group has desirably 1 to 4 carbon atoms, including acetylmethyl and propionylmethyl etc. The alkoxycarbonylmethyl groups are represented by the formula: alkyl-OCO-$CH_2$— wherein the alkyl group has desirably 1 to 4 carbon atoms, including methoxycarbonylmethyl, ethoxycarbonylmethyl and propoxycarbonylmethyl etc. The alkylsulfonyl groups are represented by the formula: alkyl-$SO_2$— wherein the alkyl group has desirably 1 to 4 carbon atoms, including methylsulfonyl, ethylsulfonyl, propylsulfonyl and isopropylsulfonyl etc.

The alkyl groups which may be fluorinated, represented by $R^2$, $R^3$ and $R^4$, have desirably 1 to 4 carbon atoms each. Such unsubstituted alkyl groups include methyl, ethyl, propyl, isopropyl, butyl and isobutyl etc. Such fluorinated alkyl groups include trifluoromethyl, 2,2,2-trifluoroethyl, 2,2,3,3,3,-pentafluoropropyl, 1-(trifluoromethyl)-2,2,2-trifluoroethyl, 2,2,3,3-tetrafluoropropyl and 2,2,3,3,4,4,4-heptafluorobutyl etc.

The alkoxy groups which may be fluorinated, represented by $R^2$, $R^3$ and $R^4$, have desirably 1 to 8 carbon atoms each. Such unsubstituted alkoxy groups include methoxy, ethoxy, propoxy, isopropoxy, butoxy, isobutoxy, pentoxy, hexyloxy, heptyloxy and octyloxy. Such fluorinated alkoxy groups include 2,2,2-trifluoroethoxy, 2,2,3,3,3,-pentafluoropropoxy, 1-(trifluoromethyl)-2,2,2-trifluoroethoxy, 2,2,3,3-tetrafluoropropoxy, 2,2,3,3,4,4,4-heptafluorobutoxy and 2,2,3,3,4,4,5,5-octafluoropentoxy.

In more detail about the compounds (I) and (II), it is particularly desirable that the ring A is unsubstituted or substituted at the 4- or 5-position with methoxy or trifluoromethyl, $R^1$ is a hydrogen atom, $R^2$ and $R^4$ are independently hydrogen atom or methyl and $R^3$ is a fluorinated alkoxy having 2 to 5 carbon atoms.

The vanadium compounds used in this invention include vanadium pentaoxide ($V_2O_5$), sodium metavanadate ($NaVO_3$), ammonium metavanadate ($NH_4VO_3$) and vanadium (IV) acetylacetonate [$(CH_3COCH_2COCH_2)_2VO$], desirably vanadium pentaoxide, sodium metavanadate and vanadium acetylacetonate.

The amount of the vanadium compounds used is generally about 0.01 to 10 mole %, desirably about 0.05 to 2 mole %, particularly desirably about 0.1 to 0.5 mole % relative to one mole of the compound (I).

Hydrogen peroxide is usually used in an aqueous solution of hydrogen peroxide, but a solution in an organic solvent such as n-butylalcohol and a solution in the mixture of said organic solvent and water may also be used. The concentration of hydrogen peroxide used is usually 10 to 70%, desirably 20 to 40%, but should not be limited only to these ranges.

The amount of hydrogen peroxide used is usually a slight excess relative to one equivalent of the compound (I), desirably about 1 to 3 equivalents, more desirably about 1 to 1.5 equivalents.

The solvents used for the reaction include halogenated hydrocarbons such as chloroform and dichloromethane, ethers such as tetrahydrofuran and dioxane, alcohols such as ethanol, methanol and isopropanol, ketones such as acetone and methylethylketone, nitriles such as acetonitrile and water, among which ethanol, methanol, acetone and acetonitrile are desirable and ethanol is more desirable. These solvents may be used singly or in combination. The amount of the solvent used for the reaction is about 0.5 to 10 l, desirably about 1 to 5 l, relative to one mole of the compound (I), but should not be limited only to these ranges.

The reaction temperature is usually the temperature under ice-cooling to about the boiling point of the solvents, usually the temperature under ice-cooling to about 40° C., more desirably about 15° to 30° C.

The reaction time is usually about 0.5 to 24 hours, desirably about 1 to 8 hours.

The desired compound (II) produced by the reaction described above is usually separated out as crystals from the reaction mixture, so that the crystals can be collected by filtration after decomposition of the excess of hydrogen peroxide remaining after the reaction by addition of an aqueous solution of sodium thiosulfate, but the crystals may also be collected by extraction with a solvent such as chloroform if necessary, followed by concentration.

The crystals thus collected can be purified if necessary by a routine method such as recrystallization and chromatography.

The starting compounds (I) can be produced by the methods described in, for example, U.S. Pat. No. 4,255,431, European Patent Laid-Open No.45200, No.74341, No.80602, No.5129, No.174726, No.175464 and Great Britain Patent Laid-Open No.2134523A, etc.

According to the method for production of this invention, 2-(2-pyridylmethylsulfinyl)benzimidazole can be obtained in a good yield (about 85% or more) and with low production of by-products such as 2-(2-pyridylmethylsulfonyl) benzimidazole N-oxide.

This invention is illustrated in more detail in the following Working Examples and Reference Example.

EXAMPLE 1

2-[[3-Methyl-4-(2,2,2-trifluoroethoxy)pyrid-2-yl]methylthio]benzimidazole (monohydrate) (1.77 g) was dissolved in dichloromethane (30 ml), to which was added dropwise at 15°–20° C. a solution of hydrogen peroxide in t-butanol (2.75 ml corresponding to 0.2 g of hydrogen peroxide) containing vanadium pentaoxide (5 mg), and then allowed to react at 20°–25° C. for about one hour. After completion of the reaction, an aqueous solution of sodium thiosulfate (0.5 g/30 ml) was added to the reaction mixture, which was stirred vigorously for about 10 minutes, allowed to stand still, and separated into layers. The dichloromethane layer was washed with water (30 ml), and concentrated under reduced pressure; to the residue was added a mixture of ethanol-water (9:1, 10 ml) for crystallization. This solution was ice-cooled, and the crystals were collected by filtration and washed with an ice-cooled mixture of ethanol-water (8:2). The crystals thus obtained were treated with a mixture of ethanol-water (9:1, 10 ml), heated (65°–70° C.) and stirred for dissolution of the crystals, then the insoluble matters were removed by hot filtration. The filtrate was ice-cooled for crystallization, and the crystals were collected by filtration, washed with ice-cooled ethanol-water mixture (8:2) and dried in vacuo to give white crystals of 2-[[3-methyl-4-(2,2,2-trifluoroethoxy)pyrid-2-yl]methylsulfinyl]benzimidazole (1.64 g). (yield: 93.2%).
m.p. 177°–178° C. (decomposed)

EXAMPLE 2

2-[[3-Methyl-4-(2,2,2-trifluoroethoxy)pyrid-2-yl]methylthio]benzimidazole (monohydrate) (10.0 g) was dissolved in ethanol (75 ml), to which was added a solution of sodium metavanadate (15 mg) in 35% aqueous solution of hydrogen peroxide (3.07 g), and allowed to react by stirring at 20°–25° for about 8 hours. After completion of the reaction an aqueous solution of sodium thiosulfate (1 g/5 ml) was added to the reaction mixture, which was stirred vigorously for about 10 minutes. The crystals were collected by filtration and washed with an ice-cooled mixture of ethanol-water (1:1). The crystals thus obtained were treated with a mixture of ethanol-water (9:1, 50 ml), heated (65°–70° C.) and stirred so that the crystals were dissolved, then the insoluble matters were removed by hot filtration. The filtrate was ice-cooled for crystallization, and the crystals were collected by filtration, washed with ice-cooled ethanol-water mixture (8:2) and dried in vacuo, to give white needles of 2-[[3-methyl-4-(2,2,2-trifluoroethoxy)pyrid-2-yl]methylsulfinyl]benzimidazole (9.0 g). (yield: 90.5%).
m.p. 177°–178° C. (decomposed)

EXAMPLE 3

2-[[3-Methyl-4-(2,2,2-trifluoroethoxy)pyrid-2-yl]methylthio]benzimidazole (monohydrate) (20.0 g) was dissolved in ethanol (150 ml), to which was added dropwise at about 20° C. a solution of vanadium pentaoxide (30 mg) in a mixture of 35% aqueous solution of hydrogen peroxide (6.14 g) and ethanol (6 ml), and allowed to react at 18°–22° for about 2.5 hours. After completion of the reaction an aqueous solution of sodium thiosulfate (2 g/60 ml) was added to the reaction mixture, which was stirred by ice-cooling for about 1 hour. The crystals were collected by filtration and washed with an ice-cooled mixture of ethanol-water (1:1). The crystals thus obtained were treated with a mixture of ethanol-water (9:1, 100 ml), heated (70°–80° C.) and stirred so that the crystals were dissolved, then the insoluble matters were removed by hot filtration. The filtrate was ice-cooled for crystallization, and the crystals were collected by filtration, washed with ice-cooled ethanol-water mixture (8:2) and dried in vacuo, to give white needles of 2-[[3-methyl-4-(2,2,2-trifluoroethoxy)pyrid-2-yl]methylsulfinyl]benzimidazole (17.8 g). (yield: 89.5%).
m.p. 177°–178° C. (decomposed)

EXAMPLE 4

Vanadium(IV) acetylacetonate (40 mg) was dissolved in ethanol (150 ml), to which 2-[[3-methyl-4-(2,2,2-trifluoroethoxy)pyrid-2-yl]methylthio]benzimidazole (monohydrate) (20.0 g) was added and then 35% aqueous solution of hydrogen peroxide (6.14 g) was added dropwise at 20°–25° C., and the mixture was allowed to react at 20°–25° C. for about 5 hours. After completion of the reaction, a solution of sodium thiosulfate (2.7 g/16 ml) was added to the reaction mixture and stirred vigorously for about 10 minutes. The crystals were collected by filtration and washed with an ice-cooled mixture of ethanol-water (8:2). The crystals thus obtained were treated with a mixture of ethanol-water (9:1, 90 ml), heated (60°–70° C.), and stirred so that the crystals were dissolved, then the insoluble matters were removed by hot filtration. The filtrate was ice-cooled for crystallization and the crystals were collected by filtration, washed with ice-cooled ethanol-water mixture (8:2) and dried in vacuo, to give white needles of 2-[[3-methyl-4-(2,2,2-trifluoroethoxy)pyrid-2-yl]methylsulfinyl]benzimidazole (18.1 g). (yield: 91.0%).
m.p. 177°–178° C. (decomposed)

EXAMPLE 5

Each 2-[[3-methyl-4-(2,2,2-trifluoroethoxy)pyrid-2-yl]methylsulfinyl]benzimidazole obtained in Examples 1–4 and in Reference Example described below was analyzed by high performance liquid chromatography (HPLC) and the following results were obtained.
Conditions of HPLC
Equipment used: Shimadzu High Performance Liquid Chromatograph Type LC-6A
Detector: Shimadzu Ultraviolet Absorption Photometer Type SPD-6A, measurement wave length: 254 nm
Data processor: Shimadzu Type CR-3A
Column: Nucleosil $5C_{18}$ (150×40 mm i.d.)
Column temperature: a fixed temperature of about 25° C.
Mobile phase: A mixture of methanol-water-triethylamine (60:40:1) of which pH has been adjusted to 7.0 by addition of phosphoric acid.
Flow rate: 0.7 ml/min.
Time required for analysis: 30 minutes

| Compound | Area percentage (%) in high performance liquid chromatography | | | | |
|---|---|---|---|---|---|
|  | Example 1 | Example 2 | Example 3 | Example 4 | Reference Example |
| sulfoxide derivative*[1] | 99.3 | 99.6 | 99.6 | 99.7 | 98.9 |
| N-oxide derivative*[2] | 0.1 | <0.1 | <0.1 | <0.1 | 0.6 |

*[1])
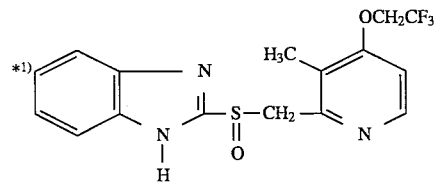

*[2])
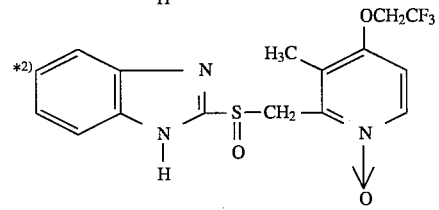

EXAMPLE 6

According to the same method as in Example 4, the following compounds were produced and analyzed by HPLC under the same conditions as in Example 5; the results are summarized as follows.

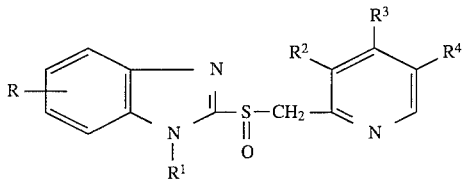

|  |  |  |  |  |  | m.p. | yield | Area percentage (%) in HPLC | |
| m | R | $R^1$ | $R^2$ | $R^3$ | $R^4$ | (°C.) | (%) | sulfoxide*[1] | N-oxide*[2] |
| --- | --- | --- | --- | --- | --- | --- | --- | --- | --- |
| 1 | H | H | $CH_3$ | $OCH_2CF_3$ | $CH_3$ | 177~178(d)* | 89 | 99.6 | <0.1 |
| 1 | 5-$CF_3$ | H | H | $OCH(CH_3)_2$ | H | 154~155(d) | 87 | 99.6 | <0.1 |
| 1 | 5-$CF_3$ | H | H | $OCH_3$ | H | 165~166(d) | 88 | 99.7 | <0.1 |
| 1 | 4-$CF_3$ | H | H | $OCH_3$ | H | 150~151(d) | 86 | 99.5 | 0.1 |
| 1 | 5-$OCH_3$ | H | $CH_3$ | $OCH_3$ | $CH_3$ | 155~156(d) | 87 | 99.7 | <0.1 |
| 1 | 5-$CH_3$ | H | $CH_3$ | $OCH_3$ | $CH_3$ | 180~181(d) | 88 | 99.7 | <0.1 |
| 1 | H | $CH_2OOCCH_3$ | $CH_3$ | $OCH_3$ | $CH_3$ | 131~133 | 85 | 99.6 | 0.1 |
| 1 | 5-F | H | H | $OCH(CH_3)_2$ | H | 145~147(d) |  |  |  |
| 2 | 5-$OCF_3$ 6-$OCF_3$ | H | $CH_3$ | $OCH_3$ | H | 184~185(d) |  |  |  |

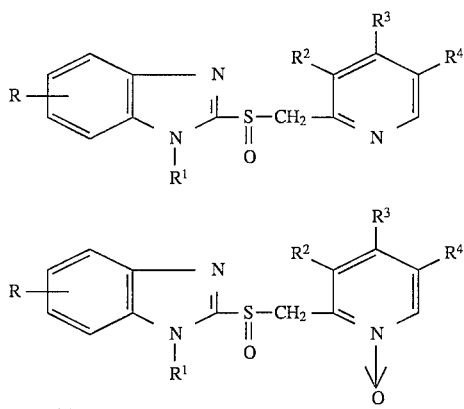

*)decomposition

Reference Example

2-[[3-Methyl-4-(2,2,2-trifluoroethoxy)pyrid-2-yl]methylthio]benzimidazole (monohydrate) (20 g) was dissolved in chloroform (200 ml), to which was added slowly dropwise below 5° C. a solution of m-chloroperbenzoic acid (13.5 g) in chloroform (200 ml), and stirred at the same temperature for about 10 minutes. After completion of the reaction, the reaction mixture was washed with a solution of sodium hydrogencarbonate, and dried over magnesium sulfate, and chloroform was evaporated off under reduced pressure. To the residue was added ethanol (100 ml) for crystallization, which was ice-cooled; the resulting crystals were collected by filtration and washed with ice-cooled ethanol. The crystals thus obtained were treated with a mixture of ethanol-water (9:1, 90 ml), heated (65°–70° C.) and stirred so that the crystals were dissolved, then the insoluble matters were removed by hot filtration. The filtrate was ice-cooled for crystallization and the crystals were collected by filtration, washed with ice-cooled ethanol-water mixture (8:2), and dried in vacuo, to give white needles of 2-[[3-methyl-4-(2,2,2-trifluoroethoxy)pyrid-2-yl]methylsulfinyl]benzimidazole (14.9 g, yield: 74.9%).

m.p. 177°–178° C. (decomposed)

What is claimed is:

1. A method for producing 2-{{3-methyl-4-(2,2,2-trifluoroethoxy)pyrid-2-yl]methylsulfinyl}benzimidazole by the selective mono-oxidation of a sulfur atom, which comprises contacting 2-{{3-methyl-4-(2,2,2-trifluoroethoxy)-pyrid-2-yl}methylthio}benzimidazole with an excess of hydrogen peroxide relative to one equivalent of the starting compound, 2-{{3-methyl-4-(2,2,2-trifluorethoxy)-pyrid-2-yl}methylthio}benzimidazole, in the presence of from about 0.01 to 10 mole % of vanadium pentaoxide, sodium metavanadate, ammonium metavanadate or vanadium (IV) acetylacetonate relative to 2-{{3-methyl-4-(2,2,2-trifluoroethoxy)-pyrid-2-yl}methylthio}benzimidazole.

2. The method according to claim 1, wherein about 1 to 3 equivalents of hydrogen peroxide is used per equivalent of 2-{{3-methyl-4-(2,2,2-trifluoroethoxy)pyrid-2-yl}methylthio}benzimidazole.

3. A method for producing 2-{(3,5-dimethyl-4-methoxypyrid-2-yl)methylsulfinyl}-5-methoxybenzimidazole by the selective mono-oxidation of a sulfur atom, which comprises contacting 2-{(3,5-dimethyl-4-methoxypyrid-2-yl)methylthio)-5-methoxybenzimidazole with an excess of hydrogen peroxide relative to one equivalent of the starting compound 2-{(3,5-dimethyl-4-methoxypyrid-2-yl)methylthio)-5-methoxybenzimidazole, in the presence of from about 0.01 to 10 mole % of vanadium pentaoxide, sodium metavanadate, ammonium metavanadate or vanadium (IV) acetylacetonate relative to 2-{(3,5-dimethyl-4-methoxypyrid-2-yl)methylthio}-5-methoxybenzimidazole.

4. The method according to claim 1, wherein about 1 to 3 equivalents of hydrogen peroxide is used per equivalent of 2-{(3,5-dimethyl-4-methoxypyrid-2-yl)methylthio}-5-methoxy-benzimidazole.

5. A method of using hydrogen peroxide as the oxidizing agent in the presence of a vanadium catalyst for the production of 2-{{3-methyl-4-(2,2,2-trifluoroethoxy)pyrid-2-yl}methylsulfinyl}benzimidazole by the selective mono-oxidation of a sulfur atom, which comprises contacting 2-{{3-methyl-4-(2,2,2-trifluoroethoxy)pyrid-2-yl}methylthio}benzimidazole with an excess of hydrogen peroxide relative to one equivalent of the starting compound, 2-{{3-methyl-4-(2,2,2-trifluorethoxy)-pyrid-2-yl}methylthio}benzimidazole, in the presence of from about 0.01 to 10 mole % of vanadium pentaoxide, sodium metavanadate, ammonium metavanadate or vanadium (IV) acetylacetonate relative to 2-{{3-methyl-4-(2,2,2-trifluoroethoxy)-pyrid-2-yl}methylthio}benzimidazole.

6. A method of using hydrogen peroxide as the oxidizing agent in the presence of a vanadium catalyst for the production of 2-{(3,5-dimethyl-4-methoxypyrid-2-yl)methylsulfinyl}-5-methoxybenzimidazole by the selective monooxidation of a sulfur atom, which comprises contacting 2-{(3,5-dimethyl-4-methoxypyrid-2-yl)methylthio)-5-methoxybenzimidazole with an excess of hydrogen peroxide relative to one equivalent of the starting compound 2-{3,5-dimethyl-4-methoxypyrid-2-yl)methylthio)-5-methoxybenzimidazole, in the presence of from about 0.01 to 10 mole % of vanadium pentaoxide, sodium metavanadate, ammonium metavanadate or vanadium (IV) acetylacetonate relative to 2-{(3,5-dimethyl-4-methoxypyrid-2-yl)methylthio}-5-methoxybenzimidazole.

\* \* \* \* \*